United States Patent [19]

Fischer et al.

[11] Patent Number: 5,747,656

[45] Date of Patent: May 5, 1998

[54] INDICATORS FOR DETERMINING THE PROTON CONCENTRATION OF STRONGLY ALKALINE AQUEOUS SOLUTIONS

[75] Inventors: Wolfgang Fischer, Darmstadt; Sylvia Baum, Griesheim; Thorsten Hartig, Gross-Zimmern; Michael Schleehahn, Lindenfels, all of Germany

[73] Assignee: Merck Patent Gesellschaft Mit Beshrankter Haftung, Darmstadt, Germany

[21] Appl. No.: 448,413

[22] PCT Filed: Sep. 21, 1994

[86] PCT No.: PCT/EP94/03156

§ 371 Date: Jun. 1, 1995

§ 102(e) Date: Jun. 1, 1995

[87] PCT Pub. No.: WO95/09894

PCT Pub. Date: Apr. 13, 1995

[30] Foreign Application Priority Data

Oct. 2, 1993 [DE] Germany .................. 43 33 696.5

[51] Int. Cl.⁶ .................. C09B 29/12; C09B 29/36; C09B 67/42; C09B 109/00

[52] U.S. Cl. .................. 534/683; 252/408.1; 436/163; 534/800

[58] Field of Search .................. 534/683, 800; 252/408.1; 436/163

[56] References Cited

U.S. PATENT DOCUMENTS 2,795,575   6/1957   Sureau et al. .................. 534/683 X
2,843,581   7/1958   Riat .................. 534/683
3,072,585   1/1963   Milionis et al. .................. 534/683 X
3,179,650   4/1965   Wehrli et al. .................. 534/683 X

FOREIGN PATENT DOCUMENTS 0287909   10/1988   European Pat. Off. .................. 534/683

*Primary Examiner*—Floyd D. Higel
*Attorney, Agent, or Firm*—Millen, White, Zelano, & Branigan, P.C.

[57] ABSTRACT

The invention relates to indicators for determine the proton concentration of strongly alkaline aqueous solutions which contain compounds of the formula (I)

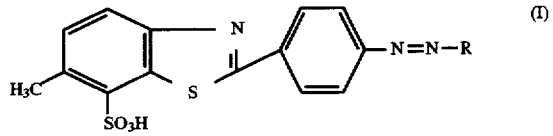

in which

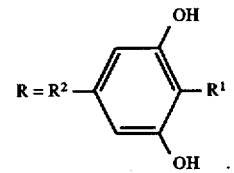

3 Claims, No Drawings

INDICATORS FOR DETERMINING THE PROTON CONCENTRATION OF STRONGLY ALKALINE AQUEOUS SOLUTIONS

This application is a 371 of PCT/EP94/03156 filed Sep. 21, 1994.

The invention relates to indicators for determining the proton concentration of strongly alkaline aqueous solutions.

The usual pH range used daily in the laboratory or even in the world around us is from pH 0 to pH 14. The usual pH papers, pH indicator sticks and pH meters are also tailored to this; they only measure in this range. In many cases, however, it is of interest to be able to determine by means of a simple indicator whether a solution present is a 1-, 3-, 5-, 7-, 9- or 11-normal alkali solution. To date, this cannot even be accomplished by a pH meter. On the contrary, a comparatively difficult titration with an acid solution must be carried out in order to determine the content.

The invention is based on the object of making available indicators with which the determination of proton concentrations in the strongly alkaline range is possible in a simple manner.

Surprisingly, it has been found that certain substantive azo dyestuffs can be employed for the purpose according to the invention.

The invention relates to indicators for determining the proton concentration of strongly alkaline aqueous solutions, which are characterized in that they contain at least one compound of the general formula (I)

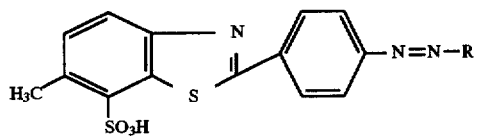

in which

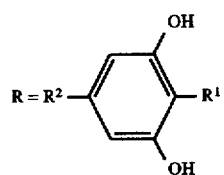

and
$R^1$=H, OH, alkyl having 1–6 C atoms, alkanoyl having 2–7 C atoms,
$R^2$=H, alkyl having 1–6 C atoms.

The indicators are preferably applied to a support.

These compounds are prepared from parent substances known in dyestuff chemistry which, from experience, impart substantive character to the dyestuffs. The parent substances carry at least one amino group, which are (sic) diazotized and coupled with phenols to give the indicators according to the invention (Ullmann, Volume A 3, 5th edition, 1985, pages 279–280). The binding position between the diazotized parent substances and the phenols can be located in all positions of the phenols not occupied by substituents.

2-(4-Aminophenyl)-6-methylbenzothiazole-7-sulfonic acid has proven particularly advantageous as a parent substance. The diazotization and subsequent coupling of the parent substance is carried out with phenol derivatives, preferably with pyrogallol, 3,5-dihydroxytoluene and 2,6-dihydroxyacetophenone.

The substances can be employed in solution like other pH indicators. More advantageously, however, materials made from cellulose, e.g. paper, films or fabric, are dyed with these substances. Because of their substantivity, the substances remain comparatively firmly stuck to these materials and are thus suitable, e.g. in strip form, directly for indicating the alkali concentration. In other embodiments, the dyed material is fixed to a colorless or white plastic film as support and can thus be assessed not only visually, but also photometrically in transmitted light or reflected light.

In order to be able to measure the alkali concentrations, a color comparison scale must be prepared beforehand. For potassium hydroxide solution and in the case of direct use of the indicator the following procedure is used:

a) Potassium hydroxide solutions of various concentrations are prepared, e.g. 1N, 2N, 4N, . . . 18N or 10%, 20%, 30% . . . 100%.

b) 1.0 mg of the indicator is dissolved in 100 ml of these solutions in each case.

c) These solutions are filled into 10 mm cuvettes, which are set up next to each other. This series is used as a color comparison scale.

1.0 mg of the indicator is dissolved in a 100 ml sample whose potassium hydroxide concentration is to be determined and the solution is filled into a 10 mm cuvette. The alkali concentration is determined by comparing the color of the cuvette containing the unknown sample with the color comparison scale. Since the concentrations of the solutions of the color comparison scale are known, the alkali concentration of the unknown sample is thus also known.

EXAMPLE 1

Preparation of an Indicator 38.4 g (120 mmol) of 2-(4-aminophenyl)-6-methyl-benzothiazole-7-sulfonic acid were dissolved in 75 ml of 2N sodium hydroxide solution and 300 ml of water. A solution of 9.1 g of sodium nitrite in 75 ml of water was added dropwise to this solution at room temperature in the course of 10 minutes and the mixture was stirred for a further 30 minutes. 300 ml of 1N hydrochloric acid were then added dropwise at 0°–5° C. and the solution containing an orange-yellow precipitate was stirred at 0°–5° C. for a further 30 minutes.

The reaction mixture was then added dropwise under nitrogen at 5°–10° C. to a solution of 21.3 g of 3,5-dihydroxytoluene (150 mmol) in 27.8 ml of 32% sodium hydroxide solution and 200 ml of ethanol (20 min), an orange-red precipitate being produced. The mixture was stirred for one hour at 5°–10° C. and then for a further 18 hours at 20°–25° C. The reaction mixture was briefly warmed and slowly added dropwise with stirring to 10 l of hot i-propanol. An orange-red precipitate was deposited, which was filtered off with suction and dried.

Yield: 34.2 g (62.5% of theory) of orange to red-brown crystals.

EXAMPLE 2

Preparation and Functioning of a Test Stick

The following two solutions were prepared:

1. 10 mg of the azo dyestuff according to Example 1 in 50 ml of water.

2. 10 mg of the azo dyestuff from 2-(4-aminophenyl)-6-methylbenzothiazole-7-sulfonic acid and 2,6-dihydroxyacetophenone in 50 ml of water.

6 mm wide and 300 mm long filter paper strips (e.g. Schleicher and Schüll No. 604) were immersed in each of these solutions and then dried. The two indicator paper strips thus obtained were stuck to a 75 mm wide, 0.2 mm thick and 300 mm long white PVC film using double-sided adhesive tape. The first zone here is directly on the edge of the film. The distance between the two zones is 3 mm. The film tape was then cut into 6 mm wide test sticks. On each test stick there were then two test zones which show the following colors in the alkaline range:

| Potassium hydroxide solution | Zone 1 | Zone 2 |
| --- | --- | --- |
| 0.1 N | yellow | yellow |
| 0.3 N | yellow | orange |
| 0.5 N | yellow | red |
| 1.0 N | yellow | red-violet |
| 4.0 N | yellow | blue-violet |
| 8.0 N | orange | blue-violet |
| 10.0 N | light red | blue-violet |
| 12.0 N | dark red | blue-violet |

As can be seen from the table, potassium hydroxide solution solution zone 2 serves as an indicator in the range between 0.1 and 4N and potassium hydroxide solution zone 1 serves as an indicator in the range between 4 and 12N. Analogous colorations were obtained using other strong bases such as sodium hydroxide solution or barium hydroxide solution if the corresponding concentrations were adjusted.

We claim:

1. A compound of the formula (I)

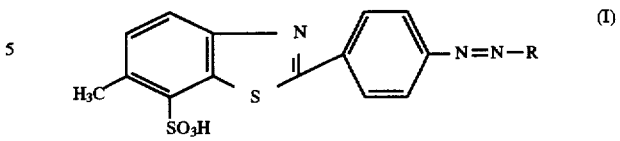

in which

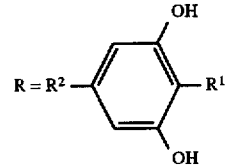

bound to formula (I) at the 1, 2, 4 or 6 position and $R^1$=H, OH, alkyl having 1–6 C atoms, alkanoyl having 2–7 C atoms, or a bond to formula (I).

$R^2$=H, alkyl having 1–6 C atoms or a bond to formula (I), wherein $R^1$ and $R^2$ both can not be H.

2. An indicator for determining the proton ($H^+$) concentration of strongly alkaline aqueous solutions, which contains at least one compound of the formula (I).

3. An indicator according to claim 2 which comprises at least one compound of formula (I) applied to a support.

* * * * *